(12) United States Patent
Tucker (10) Patent No.: US 10,987,242 B2
(45) Date of Patent: *Apr. 27, 2021

(54) APPARATUS FOR TREATING ERECTILE DYSFUNCTION AND ENHANCING PENILE ENLARGEMENT

(71) Applicant: Jerry L. Tucker, Hendersonville, NC (US)

(72) Inventor: Jerry L. Tucker, Hendersonville, NC (US)

(*) Notice: Subject to any disclaimer, the term of this patent is extended or adjusted under 35 U.S.C. 154(b) by 77 days.

This patent is subject to a terminal disclaimer.

(21) Appl. No.: 16/295,109

(22) Filed: Mar. 7, 2019

(65) Prior Publication Data

US 2019/0254862 A1 Aug. 22, 2019

Related U.S. Application Data

(63) Continuation-in-part of application No. 15/680,726, filed on Aug. 18, 2017, now Pat. No. 10,398,586.

(60) Provisional application No. 62/378,790, filed on Aug. 24, 2016.

(51) Int. Cl.
*A61F 5/41* (2006.01)

(52) U.S. Cl.
CPC .......... *A61F 5/41* (2013.01); *A61F 2005/411* (2013.01); *A61F 2005/414* (2013.01)

(58) Field of Classification Search
CPC ............................ A61F 5/41; A61F 2005/414
USPC ....................................................... 600/38–41
See application file for complete search history.

(56) References Cited

U.S. PATENT DOCUMENTS 10,398,586 B2 * 9/2019 Tucker ..................... A61F 5/41

* cited by examiner

*Primary Examiner* — John P Lacyk
(74) *Attorney, Agent, or Firm* — Chambliss, Bahner & Stophel, P.C.; Stephen D. Adams (57) ABSTRACT

An apparatus for enhancing erection of a penis includes an expandable first member that partially encircles an upper portion of the penis and partially constricts at least a first vein of the penis to reduce the volume of blood carried away from the penis via the first vein. A second member is mounted to the first member includes left and right shoulder sections configured to contact the penis shaft along the left and right sides the urethra. A contoured section is formed between and extends outwards away from the shoulders so that, when the shoulder sections contact the penis shaft and the first member encircles at least partially encircles the upper portion of the penis, the contoured section extends over and does not constrict the urethra.

5 Claims, 6 Drawing Sheets

APPARATUS FOR TREATING ERECTILE DYSFUNCTION AND ENHANCING PENILE ENLARGEMENT

CROSS-REFERENCE TO RELATED APPLICATIONS

This is a continuation-in-part application of and claims the benefit of U.S. patent application Ser. No. 15/680,726, filed on Aug. 18, 2017, which claims the benefit of U.S. Provisional Application No. 62/378,790, filed Aug. 24, 2016. Both prior applications are entitled APPARATUS FOR TREATING ERECTILE DYSFUNCTION AND ENHANCING PENILE ENLARGEMENT and are incorporated herein by reference in their entirety.

FIELD OF THE INVENTION

This invention relates to the field of medical and enhancement devices for assisting in achieving and sustaining erection of a penile organ. More particularly, this invention relates to a device for treating erectile dysfunction and enhancing penile enlargement.

BACKGROUND OF THE INVENTION

Erectile dysfunction (ED) is an ailment that impacts or inhibits a male's ability to achieve or sustain an erection of the penile organ for satisfactory sexual activity. ED may vary in severity. While some men have a total inability to achieve the erection, others have an inconsistent ability to achieve the erection or may sustain only brief erections. Over time, a variety of treatment options have been developed and are now available for men with ED. Among others, these treatment options include drugs that are administered orally, drugs that are administered directly into the penile organ, mechanical aids such as constriction rings and vacuum pumps, and surgical implants such as semi-rigid penile prosthesis, inflatable penile prosthesis, etc. Each treatment method has its own advantages and disadvantages. In addition to being used by men for treating ED, the above-described drugs and mechanical devices may also be used by men without ED who are seeking more enhanced erections. Externally-applied mechanical devices used to treat ED, such as constriction rings, may be unsafe, cause uncomfortable erections or impair ejaculation.

What is needed, therefore, is an improved method and apparatus for treating erectile dysfunction and that enhances penile enlargement.

NOTES ON CONSTRUCTION

The use of the terms "a", "an", "the" and similar terms in the context of describing the invention are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. The terms "substantially", "generally" and other words of degree are relative modifiers intended to indicate permissible variation from the characteristic so modified. The use of such terms in describing a physical or functional characteristic of the invention is not intended to limit such characteristic to the absolute value which the term modifies, but rather to provide an approximation of the value of such physical or functional characteristic.

Terms concerning attachments, coupling and the like, such as "attached", "connected" and "interconnected", refer to a relationship wherein structures are secured or attached to one another either directly or indirectly through intervening structures, as well as both moveable and rigid attachments or relationships, unless specified herein or clearly indicated by context. The term "operatively connected" is such an attachment, coupling or connection that allows the pertinent structures to operate as intended by virtue of that relationship.

The use of any and all examples or exemplary language (e.g., "such as" and "preferably") herein is intended merely to better illuminate the invention and the preferred embodiments thereof, and not to place a limitation on the scope of the invention. Nothing in the specification should be construed as indicating any element as essential to the practice of the invention unless so stated with specificity.

SUMMARY OF THE INVENTION

The above and other needs are met by a prosthetic apparatus for enhancing penile erection of a penis, where the penis includes a shaft with an upper portion and a lower portion, a urethra extending lengthwise along the lower portion of the shaft, and a first vein for carrying blood away from the penis located on top of the upper portion. The apparatus includes an expandable first member configured to at least partially encircle the upper portion of the penis and to partially constrict the first vein to reduce the volume of blood carried away from the penis via the first vein in order to enhance erection of the penis. The apparatus further includes a rigid or semi-rigid second member mounted to the first member and configured to contact a lower portion of the penis. The second member includes left and right shoulder sections configured to contact the penis shaft along the left and right sides the urethra. A contoured section is formed between and extends downwards so that, when the shoulder sections contact the bottom of the penis shaft and the first member encircles the upper portion of the penis, the contoured section extends around without constricting the urethra.

BRIEF DESCRIPTION OF THE DRAWINGS

Further advantages of the invention are apparent by reference to the detailed description when considered in conjunction with the figures, which are not drawn to scale so as to more clearly show the details, wherein like reference numbers indicate like elements throughout the several views, and wherein.

DESCRIPTION OF THE PREFERRED EMBODIMENTS OF THE INVENTION

This description of the preferred embodiments of the invention is intended to be read in connection with the accompanying drawings, which are to be considered part of the entire written description of this invention. The drawings are not necessarily to scale, and certain features of the invention may be shown exaggerated in scale or in somewhat schematic form in the interest of clarity and conciseness.

Figure 1:
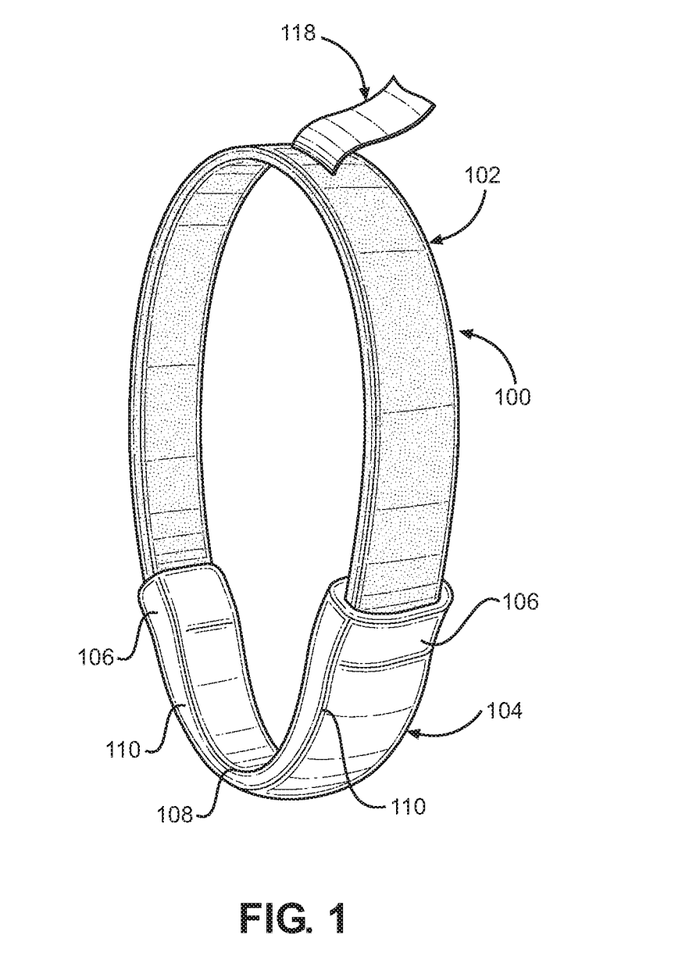
FIG. 1 is a perspective view of a prosthetic apparatus for treating erectile dysfunction having an expandable first member, a rigid or semi-rigid second member, and an installation flap.
Figure 2:
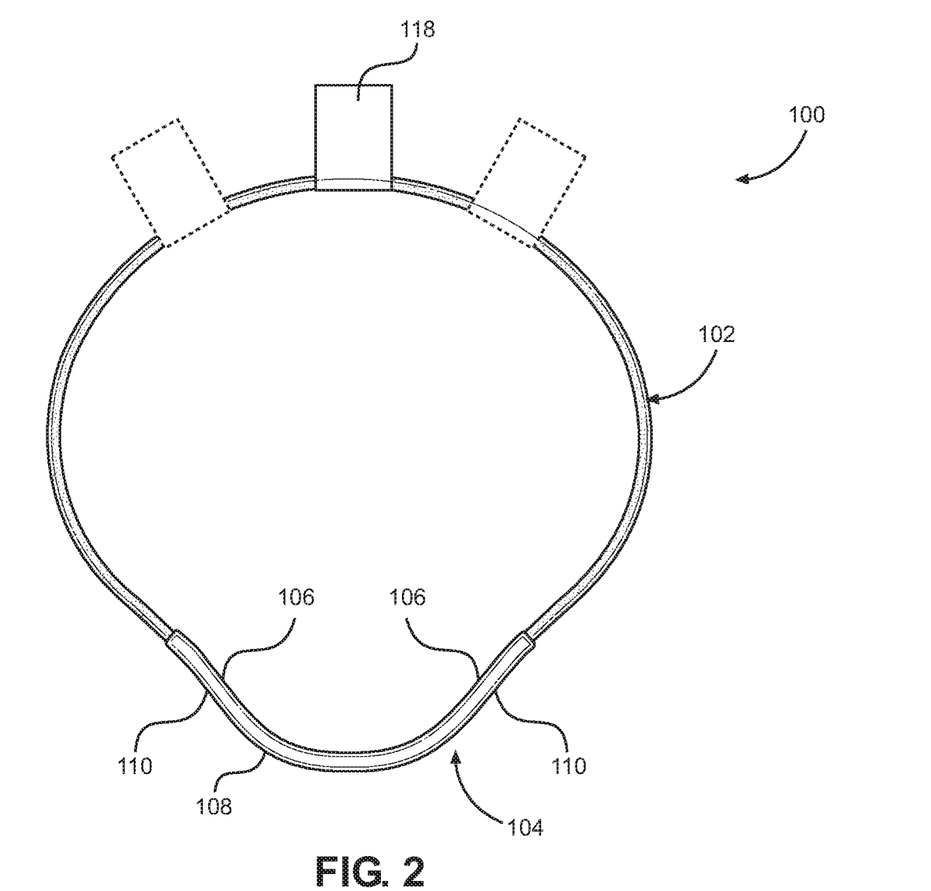
FIG. 2 is a front elevation view of the device of FIG. 1 and showing installation flaps at various optional locations.

Referring now to the drawings in which like reference characters designate like or corresponding characters throughout the several views, there is shown in FIGS. 1 and 2, a prosthetic apparatus 100 for enhancing erection of a penis. The apparatus 100 includes an expandable elastic upper member that encircles the male penis and compresses veins of the penis to reduce or eliminate venous flow of blood away from the penis, resulting in the achievement of and/or the maintaining of an erection. A rigid or semi-rigid lower member is attached to the elastic member and assists in avoiding constriction of the urethra. As the term is used herein, "rigid" means to maintain its approximate original dimension with minimal or no flexing when in use. On the other hand, "semi rigid" means to maintain its approximate dimension but with moderate flexing when in use. Among other things, avoiding constriction of the urethra can help to prevent retrograde ejaculation. Additionally, in contrast to prior devices, such as rigid penis rings, the apparatus 100 disclosed herein utilizes an expandable elastic band, which helps to eliminate the danger of necrosis of the penis by providing the user the ability of quickly removing the device, if needed.

Figure 3:
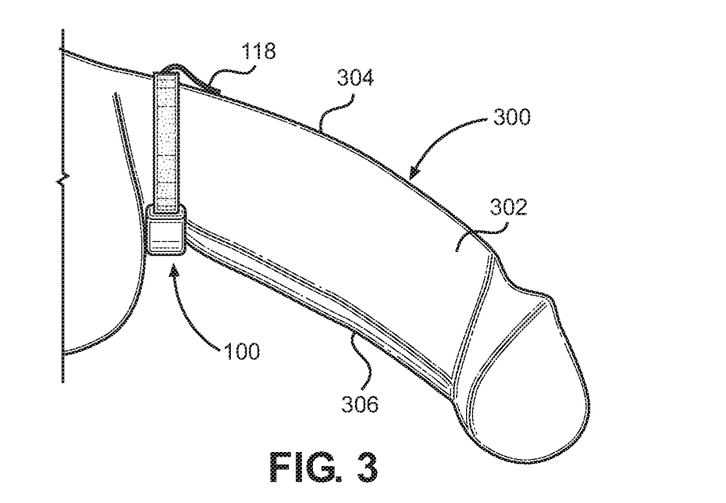
FIGS. 3 and 4 are side elevation and cross-sectional views depicting a prosthetic apparatus positioned outside the outer circumference of a partially flaccid male penis where veins within the penis are not constricted.
Figure 4:
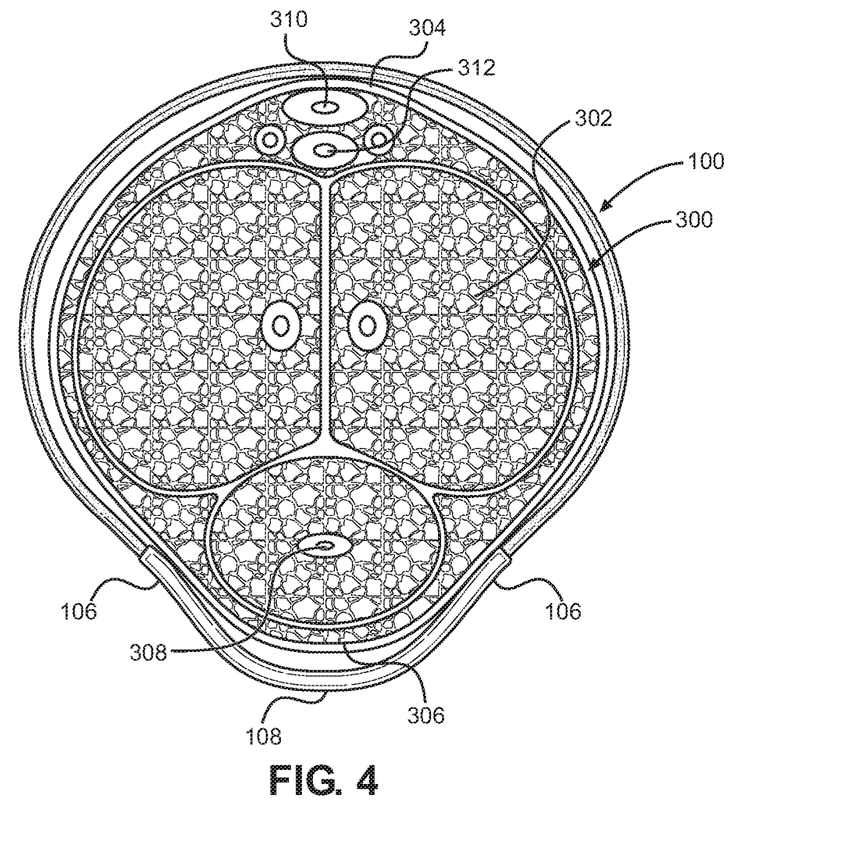

With reference to FIGS. 3 and 4, a typical penis 300 includes a shaft 302 having an upper portion 304 and a lower portion 306. A urethra 308 extends lengthwise along the lower portion of the shaft 302. A first vein 310, known as a superficial vein, for carrying blood away from the penis is located near the upper portion 304 of the shaft 302. A second vein 312, known as a deep dorsal vein, is located nearer the center of the shaft 302 between the first vein 310 and the lower portion 306. In this particular case, neither the first vein 310 nor the second vein 312 has been constricted. Accordingly, blood can freely flow into and out of the penis 300. FIGS. 3 and 4, therefore, depict the condition of a penis 300 before an apparatus 100 has been installed or after installation but while the penis remains substantially flaccid and without any constriction of the veins 310, 312.

Figure 5:
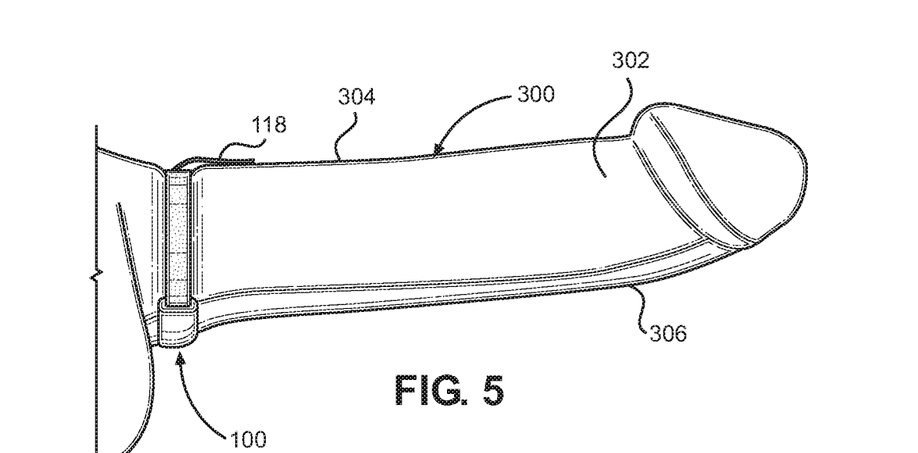
FIGS. 5 and 6 are side elevation and cross-sectional views depicting a prosthetic apparatus positioned within the outer circumference of an erect male penis where veins within the penis have been constricted.
Figure 6:
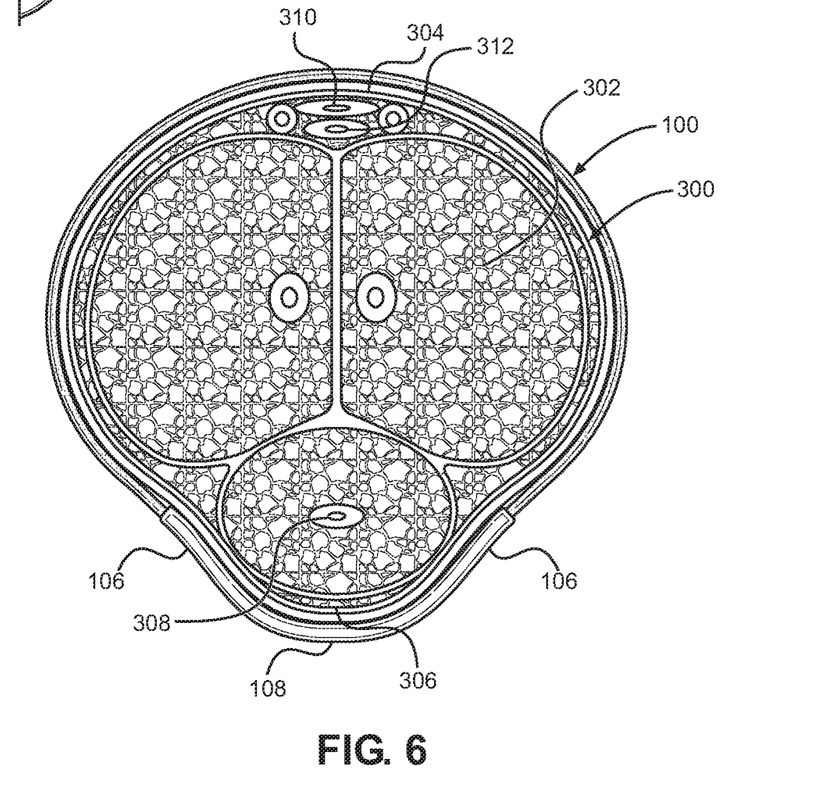

On the other, in FIGS. 5 and 6, the penis 300 has become erect. The apparatus 100 applies a force onto the penis 300 and that force has caused both of the veins 310, 312 to constrict. This constriction causes the volume of blood leaving the penis 300 to be reduced, which assists in maintaining and/or enhancing the erection. However, the device 100 is designed not to constrict and to avoid or substantially minimize pressure onto the urethra 308. Therefore, as shown best in FIG. 6, even when the veins 310, 312 are constricted, the urethra 308 is not. This allows the user to urinate and ejaculate even when the device is in place and also helps to prevent retrograde ejaculation (i.e., semen traveling incorrectly into the bladder instead of out of the body via the urethra).

The apparatus 100 shown in FIGS. 1 and 2 includes an expandable first member 102 that is mounted to a rigid or semi-rigid second member 104. The first member 102 is configured to at least partially encircle the upper portion 304 of the penis 300 and to apply pressure to partially constrict the first vein 310 to reduce the volume of blood carried away from the penis to maintain or enhance erection of the penis. In this particular case, the first member 102 fully encircles the upper portion 304 of the penis 300. The first member 102 may also be configured to, at the same time, partially constrict the second vein 312 to further reduce the volume of blood carried away from the penis to further enhance erection of the penis. This would depend on the amount of constriction force applied to the penis by the apparatus 100, which relies, in part, on the gauge and length of the expandable first member 102. As discussed further below, the first member 102 may be removed and replaced with a similar component that provides more or less constriction. Thus, the apparatus 100 is adjustable to provide more or less constriction, as desired or required.

The second member 104 is contoured and substantially conforms to the lower surface 306 of the penis 300. The second member 104 includes left and right shoulder 106 sections and a contoured section 108 that is formed between the shoulders 106. The contoured section 108 curves downwards to accommodate the lower portion of the penis. Transition sections 110, formed between the left and right shoulder sections 106 and the contoured section 108, may curve slightly inwards towards the penis 300 such that the second member 104 conforms to the lower portion 306 of the penis shaft 302. When properly installed, the device 100 is arranged so that shoulder sections 106 contact the penis shaft 302 adjacent either side of the urethra 308 and lower portion of the penis, including the urethra, is substantially located within the contoured section 108 and is not constricted when the device is in place.

Figure 7:
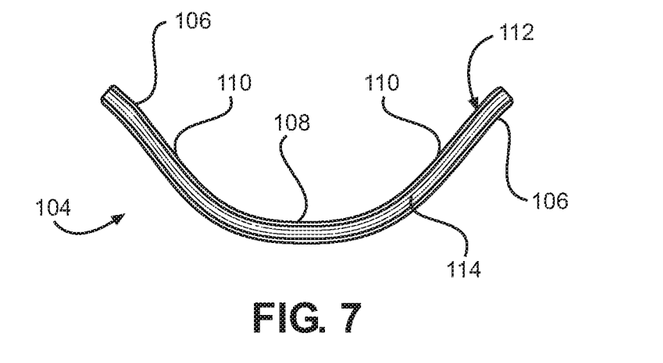
FIGS. 7 and 8 depict corresponding halves of a rigid second member having a tube construction.
Figure 8:
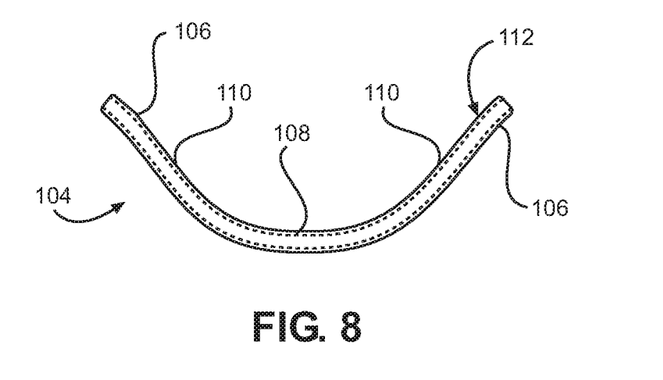

The lower member may be formed in a number of different ways that each provide different benefits, including lower cost of or ease of production, increased useful life, ease of repair, etc. For example, the second member 104 may be solid throughout and formed as bent rod-like structure. In other embodiments, shown in FIGS. 7 and 8, the second member 104 may be constructed from two corresponding half-tubes 112 that, when joined together, form a fully-enclosed tube. Each of the half tubes 112 includes a channel 114 that extends between the left and right shoulder sections 106, including through the transition section 110 and contoured sections 108, such that mounting the first half to the second half with the channels adjacent one another forms an enclosed tube configured to receive the first member. In certain embodiments, the entire enclosed tube has a circular, square, rectangular or oval-shaped cross section and a corresponding first member of the same type of cross section. In other embodiments, the first member may have cross sections different from the cross section of the second member. In certain embodiments, the first member may have any of a number of cross sections, including but not limited to, a sawtooth or wedge-shaped cross section. In other embodiments, only a portion of the enclosed tube, such as the contoured section 108 has a circular, square, rectangular or oval-shaped cross section.

Figure 9:
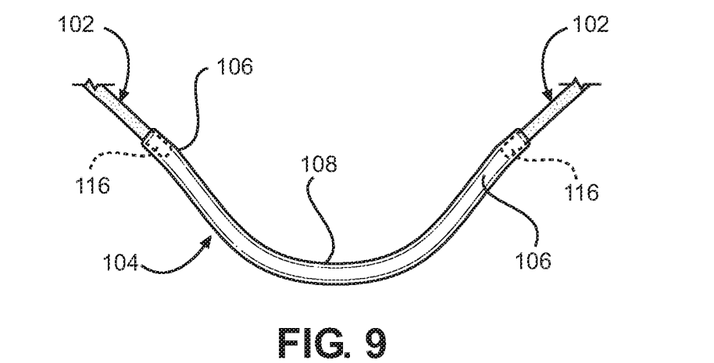
FIG. 9 depicts a rigid second member having insertion bores that receive ends of the expandable first member.
Figure 10:
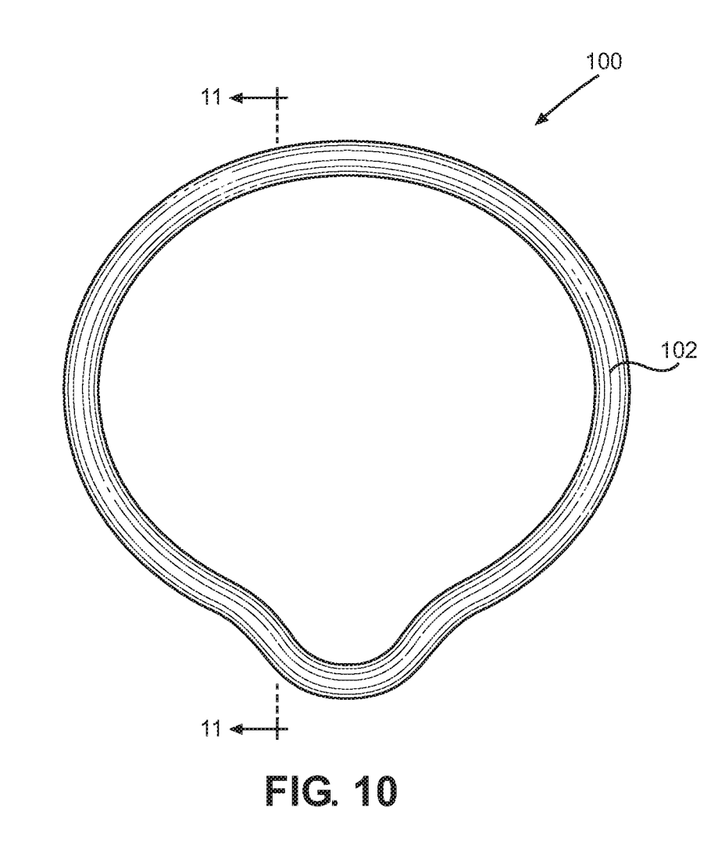
FIG. 10 is front elevation view that depicts a prosthetic apparatus for treating erectile dysfunction according to an alternative embodiment of the present invention.
Figure 11:
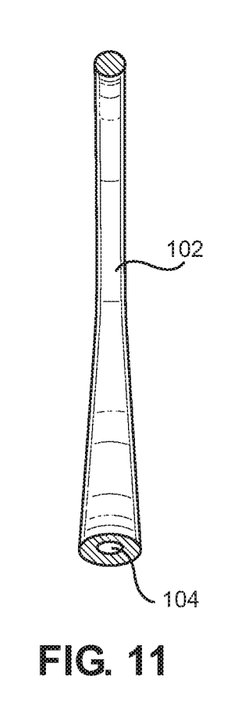
FIG. 11 is sectional view of a prosthetic apparatus taken along line 11-11 of FIG. 10.

To connect the first member 102 to the second member 104, a portion of the first member may be inserted into the channel 114. In some embodiments, the first member 102 is a continuous one-piece ring, such as an O-ring, that is inserted into a first half tube and then a second half tube is placed over the first member and mounted to the first half tube. In other cases, ends of the first member 102 may be placed into the channel 114. With reference to FIG. 9, a solid tube with insertion bores 116 formed in either end may be used as an alternative to the half tube design discussed above. The insertion bores are located in the shoulder section 106 of the second member 104 and are configured to receive ends of the first member 102. In either case, an adhesive may be used to bond the two halves of the second member 104 together and to bond the first member 102 to the second member. Other well-known connection methods (e.g., friction fitting, crimping, hooks, etc.) may also be used mount portions of the first member 102 and second member 104 together. For example, in the embodiment depicted in FIGS. 10 and 11, a solid rod-like second member 104 is encapsulated within the first member 102. In that case, the second member 104 indirectly contacts the lower portion of the penis through the first member 102. An advantage of this design is that it provides a sleek, one piece appearance that securely holds the first and second members 102, 104 together.

The first member 102 is preferably constructed of a rubber, polymer, silicon, or other material that can expand, as needed, around the circumference of an erect penis and retract when the erection subsides. For example, an O-ring or other similar device may be used for the first member 102. The first member 102 may be provided in a range of sizes, including various lengths and thicknesses (i.e., gauge, cross section). The first member 102 may be lengthened or shortened during fabrication of the device in order to increase or decrease its diameter when placed into use. Additionally, the first member 102 may have larger or smaller cross sections. The length and thickness of the first member 102 may be adjusted during fabrication of the device in order to increase or decrease the amount of compression of the apparatus 100 on the user. The most successful ring to date has had a first member 102 having a thickness of 1.5 mm in diameter, but larger and smaller sizes may be utilized in order to provide differences in flexibility and pressure applied to the penis 300. On the other hand, the second member 104 may be constructed of metal, plastic, hard rubber or other sufficiently stiff material suitable for external bodily contact. Both the first member 102 and the second member 104 may be provided in a range of colors, including various skin tone colors and decorative colors. An advantage of a user selecting a color that closely approximates his skin tone, is that the device may be nearly undetectable when being worn.

Referring again to FIGS. 1 and 2, flexible installation flaps 118 may be attached to the first member 102 to assist in the installation, adjustment, or removal of the apparatus 100. The size, number, location, ornamentation or coloring of the flexible flaps may be adjusted to suit a user's preference, to improve functionality or ease of use of the device, improve comfort, reduce visibility, etc. The flaps 118 may be constructed from a number of materials, including, for example, rubber-based tape or other suitable flexible materials.

In use, the apparatus 100 is preferably sized so that constriction of the veins 310, 312 occurs only when an erection occurs. However, different users may require differently sized components to achieve an optimal fit. Accordingly, a sizing kit may be provided that includes instructions for user to correctly size the apparatus to their anatomy. This sizing kit may include measurement tools and multiple differently-sized components to allow the user to determine the size best suited to him. Accordingly, the kit may be provided with first and second members that have different lengths, thicknesses, and cross sections. This would enable a user to create a custom-fitted device that performs optimally for their anatomy and preference.

When fitted correctly, the apparatus 100 can be worn for extended periods of time, even for days or weeks at a time. Furthermore, it can stay in place over the flaccid penis due primarily to friction between the apparatus 100 and the user's skin, with little or no constriction of the veins 310, 312. As such, the device can be worn during normal activities and does not require removal when not in use like prior devices. Wearing the device 100 on a continual basis would enable a user to participate in sexual activity without the delay of waiting for the effects of a pill to take effect or to install another device.

The device 100 may be used in conjunction with erection enhancing drugs in order to further develop the erection of the user. This is especially useful if the user typically experiences venous leakage even when using such drugs, because the device 100 will suppress or eliminate such leakage.

The device 100 may be used in conjunction with a condom. While it may be fitted over a condom it is preferable to install the device 100 on the penis 300 first and then place the condom over it in order to minimize the possibility of rupturing the condom. An advantage of the device 100 is that it may be installed prior to engaging in sexual activity. However, in certain embodiments, the device 100 may be formed as an integral part of the condom such that the device and condom are simultaneously installed.

An additional advantage of the device 100 is that it is virtually undetectable to a user's partner when in use. As shown best in FIG. 5, with the exception of the optional installation flap 118, the device 100 is designed to sit at or below the user's skin level when in use. As such, the device does not protrude above the surface of the penis 300. Thus, the device is nearly undetectable, especially when the device 100 matches the user's skin color. In contrast, other penile constriction rings typically reside outside the outer circumference of the penis and are obvious to the user and his partner.

Although this description contains many specifics, these should not be construed as limiting the scope of the invention but as merely providing illustrations of some of the presently preferred embodiments thereof, as well as the best mode contemplated by the inventor of carrying out the invention. The invention, as described herein, is susceptible to various modifications and adaptations as would be appreciated by those having ordinary skill in the art to which the invention relates.

What is claimed is:

1. A method for enhancing erection of a penis, where the penis includes a shaft with an upper portion and a lower portion, a urethra extending lengthwise along the lower portion of the shaft, and a first vein for carrying blood away from the penis located between the upper and lower portions, the method comprising the steps of:
   providing an apparatus having an expandable first member and a second member that is at least semi-rigid and that has left and right shoulder sections and a contoured section formed between and curving away from the shoulder sections;
   placing the apparatus onto said penis such that the first member at least partially encircles the upper portion of the penis while, at the same time, the second member contacts the penis shaft along the left and right sides of the urethra so that the first member partially constricts the first vein in order to reduce the volume of blood carried away from the penis and to enhance erection of the penis while the contoured section extends around and does not constrict the urethra.

2. The method of claim 1 wherein the second member is entirely encapsulated within the first member such that the second member does not directly contact the penis.

3. The method of claim 1 wherein the apparatus includes an installation flap mounted to the first portion and the method further comprises the step of grasping and pulling the installation flap to facilitate installation, adjustment, and removal of the apparatus.

4. A method for constructing a device for enhancing erection of a penis, where the penis includes a shaft with an upper portion and a lower portion, a urethra extending lengthwise along the lower portion of the shaft, and a first vein for carrying blood away from the penis located between the upper and lower portions, the method comprising the steps of:

providing an expandable first member;

providing an elongate second member having left and right shoulder sections and a contoured section formed between the shoulder sections;

attaching a portion of the first member to each of the left and right shoulder sections of the second member such that the first member can partially encircle the upper portion of the penis while, at the same time, the second member contacts the penis shaft along the left and right sides of the urethra to enable the first member to partially constrict the first vein to reduce the volume of blood carried away from the penis in order to enhance erection of the penis while the contoured section extends around and does not constrict the urethra.

5. The method of claim 3 further comprising the step of entirely encapsulating the second member within the first member.

* * * * *